United States Patent [19]
Watanabe et al.

[11] Patent Number: 5,455,268
[45] Date of Patent: Oct. 3, 1995

[54] ESCULETIN DERIVATIVES AND PHARMACEUTICAL COMPOSITION

[75] Inventors: Koju Watanabe; Koichi Niimura, both of Saitama; Kiyonori Umekawa, Chiba, all of Japan

[73] Assignee: Kureha Chemical Industry Co., Ltd., Tokyo, Japan

[21] Appl. No.: 204,445

[22] Filed: Mar. 2, 1994

[30] Foreign Application Priority Data

Mar. 2, 1993 [JP] Japan .................................. 5-066164
Dec. 27, 1993 [JP] Japan .................................. 5-351659

[51] Int. Cl.⁶ .................................................. A61K 31/35
[52] U.S. Cl. .......................... 514/457; 549/285; 514/825
[58] Field of Search ........................ 549/285; 514/459, 514/825

OTHER PUBLICATIONS

Chandratre et al., "Studies in Synthesis of Furocoumarins: Part XXVIII—Synthesis of Difuranocoumarins," *Indian J. Chem.*, vol. 268, No. 12, pp. 1148–1150 (Dec. 1987).
Nagarajan et al., "Coumarins of *Fraxinus floribunda*," *Indian J. Pharm. Sci.*, vol. 46, No. 5, pp. 176–177 (1984).
*Chemical Abstracts*, vol. 76, No. 15, Abstract No. 81680r (1972).
*Chemical Abstracts*, vol. 100, No. 27, Abstract No. 6270t (1984).
*Chemical Abstracts*, vol. 99, Abstract No. 187316 (1983).
*Chemical Abstracts*, vol. 99, Abstract No. 187317 (1983).
*Chemical Abstracts*, vol. 99, Abstract No. 18718 (1983).

Primary Examiner—Alan L. Rotman
Assistant Examiner—Amelia Owens
Attorney, Agent, or Firm—Sughrue, Mion, Zinn, Macpeak & Seas

[57] ABSTRACT

A pharmaceutical composition comprising a compound of the general formula (I):

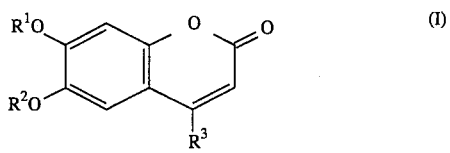

wherein $R^1$ and $R^2$ are, independently, a hydrogen atom, a saturated or unsaturated aliphatic acyl having 2 to 25 carbon atoms or benzoyl group and $R^3$ is a hydrogen atom or alkyl group, and a pharmaceutically acceptable carrier is disclosed. Further, a novel compound of the general formula (I) wherein $R^1$ and $R^2$ are, independently, a hydrogen atom, pivaloyl, capryloyl, lauroyl, palmitoyl, stearoyl, linoleoyl, docosahexaenoyl, or benzoyl group, and $R^3$ is a hydrogen atom or methyl group, is also disclosed.

16 Claims, No Drawings

ESCULETIN DERIVATIVES AND PHARMACEUTICAL COMPOSITION

BACKGROUND OF THE INVENTION

1. Field of the Invention

The present invention relates to novel esculetin derivatives and pharmaceutical compositions, more particularly an agent for protecting cartilage, i.e., a chondroprotective agent.

2. Description of the Related Art

There are various types of arthropathy, for example, rheumatoid arthritis, rheumatic fever, and osteoarthritis. Many people particularly suffer from rheumatoid arthritis and osteoarthritis, and these diseases are considered the major types of arthropathy. There are congenital and secondary osteoarthritis, and further primary osteoarthritis caused by degeneration of the articular cartilage along with aging. Patients suffering from primary osteoarthritis have recently been increasing along with the increase in the population of the aged.

Although there are considerable differences of the causes and conditions between rheumatoid arthritis and osteoarthritis, the articular function becomes eventually obstructed by the destruction of the cartilage in both of rheumatoid arthritis and osteoarthritis.

The first choice of medicines for treatment of rheumatic diseases, such as rheumatoid arthritis, rheumatic fever, systemic lupus erythematosus, or osteoarthritis, are analgesic and anti-inflammatory agents, for example, aspirin or indomethacin. Further, gold compounds (for example, Shiosol), immunomodulators, steroids, or D-penicillamine is used as the medicine for treatment of rheumatoid arthritis.

The above conventional analgesic and anti-inflammatory agents, however, were not effective against the destruction of the articular cartilage, and in fact, sometimes exhibited adverse effect in the experiments using chondrocytes. Further, no function to suppress the destruction of articular cartilage was found in the above medicines for treatment of rheumatoid arthritis.

It was known that esculetin and 4-methylesculetin exhibit the function to reduce cholesterol level, strengthening the veins, and anti-oxidation (Japanese Examined Patent Publication No. 42-16626). Further, it was also known that diesters of 4-methylesculetin with carboxylic acids having 6 to 25 carbon atoms, particularly, diesters of caprylic, lauric or palmitic acid exhibit an effective anti-inflammatory action in the treatment of skin disease (FR 2276819). However, it was not known that the above esculetin and esculetin derivatives exhibit a function to suppress cartilage destruction.

SUMMARY OF THE INVENTION

The inventors found that esculetin compounds, namely, esculetin and esculetin derivatives, showed significant inhibition of the depletion of proteoglycan which is a major component of the cartilage matrix, and therefore, are useful as a chondroprotective agent for prohibiting the destruction of the articular cartilage. Further, the above esculetin compounds involve some novel compounds.

Accordingly, the object of the present invention is to provide a pharmaceutical composition, particularly, a chondroprotective agent, comprising an esculetin compound as an effective ingredient.

Another object of the present invention is to provide a novel esculetin derivative.

The present invention relates to a pharmaceutical composition, particularly a chondroprotective agent, comprising a compound of the general formula (I):

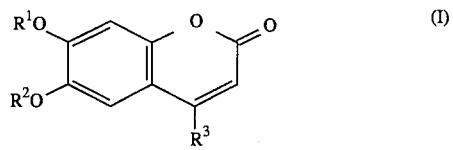

wherein $R^1$ and $R^2$ are, independently, a hydrogen atom, a saturated or unsaturated aliphatic acyl having 2 to 25 carbon atoms or benzoyl group and $R^3$ is a hydrogen atom or alkyl group [hereinafter referred to as the present compound (I)].

Further, the present invention relates to a compound of the general formula (II):

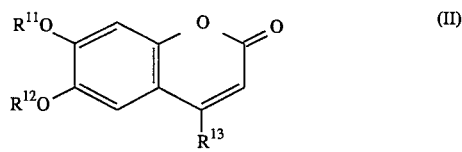

wherein $R^{11}$ and $R^{12}$ are independently a hydrogen atom, pivaloyl, capryloyl, lauroyl, palmitoyl, stearoyl, linoleoyl, docosahexaenoyl, or benzoyl group and $R^{13}$ is a hydrogen atom or methyl group [hereinafter referred to as the present compound (II)].

The present compound (II) is novel, and encompassed in the scope of the present compound (I) exhibiting the cartilage protecting function. Therefore, in the present specification, the following explanation regarding the present compound (I) may also be applied to the present compound (II), if applicable.

DESCRIPTION OF THE PREFERRED EMBODIMENTS

In the present compound (I), preferred examples of the groups $R^1$ and $R^2$ are a hydrogen atom, acetyl, pivaloyl, capryloyl, lauroyl, palmitoyl, stearoyl, linoleoyl, docosahexaenoyl and benzoyl group, and more preferred examples are the groups $R^{11}$ and $R^{12}$ defined in the present compound (II), namely, a hydrogen atom, pivaloyl, capryloyl, lauroyl, palmitoyl, stearoyl, linoleoyl, docosahexaenoyl, or benzoyl group. Particularly preferred examples of the groups $R^1$ and $R^2$ or groups $R^{11}$ and $R^{12}$ in the present compounds (I) and (II) are a hydrogen atom, pivaloyl, stearoyl, and benzoyl group. The examples of the group $R^3$ are preferably a hydrogen atom and a lower alkyl group having 1 to 4 carbon atoms, more preferably the group $R^{13}$ in the present compound (II), namely, a hydrogen atom or methyl group.

The examples of the present compounds (I) and (II) are as follows:

esculetin, 4-methylesculetin, esculetin 6,7-bis(acetate), 4-methylesculetin 6,7-bis(acetate), esculetin 6,7-bis(pivalate), 4-methylesculetin 6,7-bis(pivalate), esculetin 6-monopivalate, 4-methylesculetin 6-monopivalate, esculetin 7-monopivalate,
4-methylesculetin 7-monopivalate,
esculetin 6,7-bis(caprylate),
4-methylesculetin 6,7-bis(caprylate),
esculetin 6,7-bis(laurate),
4-methylesculetin 6,7-bis(laurate),
esculetin 6,7-bis(palmitate),
4-methylesculetin 6,7-bis(palmitate),
esculetin 6,7-bis(stearate),
4-methylesculetin 6,7-bis(stearate),
esculetin 6,7-bis(linoleate),
4-methylesculetin 6,7-bis(linoleate),
esculetin 6,7-bis(docosahexaenoate),
4-methylesculetin 6,7-bis(docosahexaenoate),
esculetin 6,7-bis(benzoate),
4-methylesculetin 6,7-bis(benzoate)

Of the above-mentioned compounds, esculetin 6-monopivalate, esculetin 6,7-bis(pivalate), esculetin 6,7-bis(stearate), 4-methylesculetin 6,7-bis(stearate), 4-methylesculetin 6,7-bis(linoleate), 4-methylesculetin 6,7-bis(docosahexaenoate), and -methylesculetin 6,7-bis(benzoate) are the typical examples of the present compound (II) and are novel.

Esculetin and 4-methylesculetin are commercially available as reagents. For example, esculetin is purchased from the Tokyo Kasei Kogyo K.K., Japan, and 4-methylesculetin is purchased from the Sigma Chemical Company, (St. Louis, Mo.).

The various mono or diesters of carboxylic acids with esculetin or 4-alkylesculetin may be prepared by reacting esculetin or 4-alkylesculetin and various carboxylic acids according to the following processes:

1) Esculetin or 4-alkylesculetin and a carboxylic acid are reacted in a suitable solvent in the presence of an acid catalyst, for example, an inorganic acid, such as hydrochloric, sulfuric or phosphoric acid or an organic acid, such as acetic or p-toluene sulfonic acid.
2) Esculetin or 4-alkylesculetin and a carboxylic acid are reacted in an organic solvent, for example, dimethylformamide, acetone, dioxane, acetonitrile, chloroform, methylene chloride, tetrahydrofuran, or pyridine in the presence of a condensing agent, for example, dicyclohexylcarbodiimide, N,N'-carbonyldi(2-methylimidazole), diphenylketene-N-cyclohexylimine, alkoxyacetylene, polyphosphoric acid ethyl ester, thionyl chloride, or oxalyl chloride, usually while cooling or at room temperature.
3) Esculetin or 4-alkylesculetin and an acid anhydride are reacted in the presence of a basic compound, for example, triethylamine, pyridine, 4-(N,N-dimethylamino)pyridine, or diethylmethylamine.
4) Esculetin or 4-alkylesculetin and an acid halide (acyl halide, such as chloride or bromide) are reacted in a solvent to which a basic compound, for example, triethylamine, pyridine, 4-(N,N-dimethylamino)pyridine or diethylmethylamine, or in a basic solvent, for example, pyridine.

In the above processes, the monoester or diester is formed depending on the ratio of the starting materials used. When the carboxylic acid, acid anhydride, or acid halide is used in an equimolar amount or a small excess amount to that of esculetin or 4-alkylesculetin used, the monoester may be prepared, whereas when the carboxylic acid, acid anhydride, or acid halide is used in a large excess amount, usually in double the molar ratio or more, the diester may be prepared.

In the latter case, a mixture of the diester and monoester may sometimes be obtained. In this case, it is possible to easily separate the resulting diester and monoester by a conventional separation method such as chromatography.

As the method to purify the reaction product, extraction, chromatography, recrystallization, or reprecipitation may be used. The structure of the purified product may be confirmed by the infrared absorption spectrum, ultraviolet absorption spectrum, nuclear magnetic resonance absorption spectrum, elemental analysis, or mass spectrum.

The toxicity of the present compound (I) was examined. Typical examples of the present compound (I) were administered intraperitoneally at a dose of 750 mg/kg (body weight) to male mice continuously for four days. No deaths and no remarkable toxicity were observed. The present compound (I) is extremely safe (see Example 2).

The present compound (I) exhibits, as a pharmacological effect, the function to inhibit destruction of chondrocyte matrix in cultured chondrocytes (derived from cartilage of rabbit shoulder and knee joints) (see Example 3).

Accordingly, the present compound (I) is useful as a chondroprotective agent for treating various types of arthropathy accompanying the cartilage destruction of the joints. Examples of such arthropathy include rheumatoid arthritis, osteoarthritis, periarthritis humeroscapularis, shoulder-arm-neck syndrome, lumbago, etc.

The pharmaceutical composition, particularly the chondroprotective agent containing the present compound (I) as an effective ingredient may be in the form of any conventional formulation. The pharmaceutical composition may contain the present compound (I) alone, or a mixture of the present compound (I) with any pharmaceutically acceptable carrier or diluent. The pharmaceutical composition may contain the effective ingredient in an amount of 0.01 to 100 percent by weight, preferably 0.1 to 70 percent by weight.

The chondroprotective agent of the present invention may be administered orally or parenterally.

The dose of the pharmaceutical composition, particularly the chondroprotective agent according to the present invention varies with the patient (animal or human), age, individual differences, state of illness, and the like. Generally speaking, however, when a human is treated, the dose of oral administration of the present compound (I) is in the range of 0.1 to 500 mg/kg (body weight) per day, preferably 0.5 to 200 mg/kg (body weight), which is usually divided into 1 to 4 dosage in a day, although the dose outside the above range may sometimes be administered.

EXAMPLES

The present invention now will be further illustrated by, but is by no means limited to, the following Examples. In the following Examples, TLC means thin layer chromatography.

Example 1: Preparation of the Present Compound (I) or (II)

(1) Preparation of esculetin 6,7-his(acetate)

Esculetin (Tokyo Kasei; 890 mg, 5 mmol) and 4-(N,N-dimethylamino)pyridine (1.528 g, 12.5 mmol) were put into an eggplant type flask (50 ml), and then, methylene chloride (10 ml) was added to give a suspension. To the resulting suspension, acetyl chloride (Wako Pure Chemicals; 918 mg, 12.5 mmol) was added dropwise at 10° C. The reaction was exothermic. After the reaction mixture was stirred at 10° C. for 2 hours, white precipitates were obtained. Methylene chloride (25 ml) was added to thereby completely dissolve the formed precipitate.

After the end of the reaction had been confirmed, distilled water (40 ml) was added to the reaction solution. The resulting solution was extracted with methylene chloride (25 ml×2). The collected organic layers were washed with distilled water (20 ml ×1), and dried over sodium sulfate. Then, the solvent was evaporated by a rotary evaporator to obtain a crystalline crude product (1.265 g). The crude product was recrystallized from ethyl alcohol to obtain the above-titled compound (1.03 g, yield=78.6%) as a colorless needle shaped crystal.

Melting point: 133°–133.5° C.

TLC: Rf 0.33 (n-hexane/ethyl acetate 1:1)

$^1$H-NMR (CDCl$_3$, δ ppm): 2.32 (s, 3H, Ac), 2.33 (s, 3H, Ac), 6.43 (d, 1H, J=9.62 Hz, C3-H), 7.22 (s, 1H), 7.35 (s, 1H), 7.64 (d, 1H, J=9.62 Hz, C4-H)

IR (KBr, νmax): 1778s, 1738s, 1636m, 1570m, 1510m, 1436m, 1378m, 1218s, 1128s (2) Preparation of 4-methylesculetin 6,7-bis(acetate)

The procedure of Example 1(1) was repeated, except that 4-methylesculetin (Sigma Chemical Company) was used as a starting material. The above-titled compound was obtained as a yellow crystal.

$^1$H-NMR (CDCl$_3$, δ ppm): 7.33 (s, 3H), 7.40 (s, 3H), 6.32 (s, 1H), 7.24 (s, 1H), 7.44 (s, 1H)

(3) Preparation of esculetin 6,7-bis(acetate)

Esculetin (890 mg, 5 mmol) and 4-(N,N-dimethylamino)pyridine (1.528 g, 12.5 mmol) were put into an eggplant type flask (50 ml), and then, methylene chloride (20 ml) was added to give a suspension. To the resulting suspension, stearoyl chloride (Tokyo Kasei; 3.787 g, 12.5 mmol) was added dropwise at 10° C. The reaction mixture became turbid to white, and then, was solidified. Thereafter, methylene chloride (20 ml) was added to the resulting reaction mixture to give a suspension. The resulting suspension was stirred at room temperature for 5 hours. After the end of the reaction had been confirmed, the reaction mixture was poured into ice water (20 ml). The resulting mixture was extracted with methylene chloride (100 ml×1). The separated organic layer was washed with distilled water (20 ml×1) and dried over sodium sulfate. Then, the solvent was evaporated by a rotary evaporator to obtain a white crude product (3.91 g). The crude product was recrystallized from methylene chloride/n-hexane to obtain the above-titled compound (2.773 g; yield=78.0%) as a white powdery crystal.

Melting point: 85°–860° C.

$^1$H-NMR (CDCl$_3$, δ ppm): 0.88 (t, 6H, CH$_3$), 1.26 (m, 56H, CH$_2$), 1.72 (m, 4H, CH$_2$), 2.55 (q, 4H, CH$_2$CO), 6.42 (d, 1H, C3-H), 7.21 (s, 1H, aromatic), 7.33 (s, 1H, aromatic), 7.63 (d, 1H, C4-H)

(4) Preparation of 4-methylesculetin 6,7-bis(stearate)

The procedure of Example 1 (3) was repeated, except that 4-methylesculetin was used as a starting material. The above-titled compound was obtained as a white crystal.

Melting point: 121°–1220° C.

$^1$H-NMR (DMSO, δ ppm): 0.85 (t, 6H, CH$_3$), 1.24 (m, 56H, CH$_2$), 1.48 (m, 2H, CH$_2$), 1.64 (m, 2H, CH$_2$), 2.18 (m, 2H, CH$_2$), 2.34 (s, 3H, C4-CH$_3$), 2.57 (m, 2H, CH$_2$), 6.18 (s, 1H, C3-H), 6.84 (s, 1H, aromatic), 7.42 (s, 1H, aromatic)

(5) Preparation of 4-methylesculetin 6,7-bis(linoleate)

The procedure of Example 1(4) was repeated, except that linoleoyl chloride (Tokyo Kasei) was used instead of stearoyl chloride. The above-titled compound was obtained as a yellow oil.

$^1$H-NMR (CDCl$_3$, δ ppm): 0.90 (t, 6H), 1.2 to 1.4 (m, 32H), 1.4 to 2.0 (m, 4H), 2.0 to 2.2 (m, 8H), 2.4 (s, 1H), 2.8 (t, 4H), 5.3 to 5.5 (m, 8H), 6.3 (s, 1H), 7.2 (s, 1H), 7.4 (s, 1H)

(6) Preparation of 4-methylesculetin 6,7-bis(docosahexaenoate)

The procedure of Example 1 (4) was repeated, except that docosahexaenoyl chloride (Tokyo Kasei; docosa-4,7,10,13,16,19-hexaenoyl chloride) was used instead of stearoyl chloride. The above-titled compound was obtained as a yellow oil.

$^1$H-NMR (CDCl$_3$, δ ppm): 0.95 (t, 6H), 2.10 (m, 4H), 2.2 (s, 3H), 2.4 to 2.7 (m, 8H), 2.7 to 3.0 (m, 12H), 5.3 to 5.7 (m, 24H), 6.3 (s, 1H), 7.2 (s, 1H), 7.4 (s, 1H)

(7) Preparation of esculetin 6,7-bis(benzoate)

Esculetin (890 mg, 5 mmol) and 4-(N,N-dimethylamino)pyridine (1.528 g, 12.5 mmol) were put into an eggplant type flask (50 ml), and then methylene chloride (10 ml) was added to give a suspension. To the suspension, benzoyl chloride (Tokyo Kasei, 1.757 g, 12.5 mmol) was slowly added dropwise at 10° C. White precipitates were immediately formed. The reaction mixture was stirred at room temperature for 4 hours.

After the reaction had been completed, the reaction mixture was poured into ice water (20 ml), and then, extracted with methylene chloride (20 ml×3). The collected organic layers were washed with distilled water (20 ml×1), dried over sodium sulfate, then the solvent was evaporated by a rotary evaporator to obtain a crystalline crude product (2.136 g). The crude product was recrystallized from methylene chloride/n-hexane to obtain the above-titled compound (1.899 g, yield=98.4%) as a white powdery crystal.

Melting point: 183°–184.5° C.

TLC: Rf 0.69 (n-hexane/ethyl acetate 1:1)

$^1$H-NMR (CDCl$_3$, δ ppm): 6.47 (d, 1H, J=9.62Hz), 7.38 (m, 6H, aromatic), 7.44 (s, 1H), 7.56 (s, 1H), 7.71 (d, 1H, J=9.62Hz), 8.04 (m, 4H, aromatic)

IR (KBr, νmax): 1765s, 1745s, 1625w, 1605w, 1570w, 1510m, 1475m, 1430m, 1390m, 1325w, 1255s (8) Preparation of 4-methylesculetin 6,7-bis(benzoate)

4-methylesculetin (960 mg, 5 mmol) and 4-(N,N-dimethylamino)pyridine (2.445 g, 20 mmol) were put into an eggplant type flask (50 ml), and then, methylene chloride (10 ml) was added to give a suspension. To the resulting suspension, benzoyl chloride (2.811 g, 20 mmol) was slowly added dropwise at 10° C. White precipitates were immediately formed. The reaction mixture was stirred at room temperature for 4 hours.

After the reaction had been completed, the reaction mixture was poured into ice water (20 ml), and then extracted with methylene chloride (20 ml×3). The collected organic layers were washed with distilled water (20 ml×1), dried over sodium sulfate, then the solvent was evaporated by a rotary evaporator to obtain a crystalline crude product (2.250 g). The crude product was recrystallized from methylene chloride/n-hexane to obtain the above-titled compound (1.960 g, yield=98.0%) as a white powdery crystal.

Melting point: 146°–152° C.

$^1$H-NMR(CDCl$_3$, δ ppm): 2.41 (d, 3H, J=2.0Hz), 6.34 (d, 1H, J=2.0Hz), 7.33 to 7.64 (m, 8H), 8.00 (d, 2H, J=2.6Hz), 8.09 (d, 2H, J=2.3Hz).

(9) Preparation of esculetin 6,7-bis(pivalate) (I) and esculetin 6-monopivalate (II)

Esculetin (200 mg, 1.12 mmol) and pyridine (3 ml) were put into an eggplant type flask (50 ml). To the mixture, pivaloyl chloride (283.6 rag, 2.35 mmol) was added at 0° C., and then the mixture was stirred at room temperature for 26 hours.

Thin layer chromatography was used to confirm the disappearance of the starting material and the formation of the two products (Rf=0.8 and 0.23, methylene chloride/ methanol= 9:1). Then, the reaction mixture was poured into ice water (10 ml) and extracted with ether. The collected organic layers were dried over sodium sulfate and concentrated under reduced pressure to obtain a crude product.

The crude product was separated and purified by silica gel chromatography. Methylene chloride was used to obtain the above-titled compound (I) as the first effluent (colorless crystal, yield=72%) and the above-titled compound (II) as the second effluent (colorless crystal, yield=25%).

Above-titled compound (I)
Melting point: 148°–149° C.
$^1$H-NMR (90 MHz, CDCl$_3$, δ ppm): 1.35 (s, 18H), 6.40 (d, 1H, J=10.3Hz), 7.15 (s, 1H), 7.29 (s, 1H), 7.64 (d, 1H, J=10.3Hz)

Above-titled compound (II)
Melting point: 159°–162° C.
$^1$H-NMR (90 MHz, CDCl$_3$, δ ppm): 1.39 (s, 9H), 6.26 (d, 1H, J=9.5Hz), 6.98 (s, 1H), 7.18 (s, 1H), 7.60 (d, 1H, J=9.5Hz)

Example 2: Mice Toxicity Test via Intraperitoneal Administration for Four Days

A suspension of esculetin or esculetin 6,7-bis(benzoate) in 0.5% methylcellulose aqueous solution was intraperitoneally administered to 6 week-old Crj:CD-1 (ICR) male mice (five mice in a group) once a day for four days at the dose of 750 mg/kg. No deaths and no remarkable toxicity were observed in both of the above compounds.

The same toxicity test was performed on 4-methylesculetin, esculetin 6,7-bis(acetate), 4-methylesculetin 6,7-bis(acetate), esculetin 6,7-bis(stearate), 4-methylesculetin 6,7-bis(stearate), 4-methylesculetin 6,7-bis(linoleate), 4-methylesculetin 6,7-bis(docosahexaenoate), 4-methylesculetin 6,7-bis(benzoate), esculetin 6,7-bis(pivalate), and esculetin 6-monopivalate, but no deaths were observed.

Example 3: Effect of test compounds on Proteoglycan Depletion in Chondrocyte Culture (a) Preparation of cultured chondrocytes Cartilages were taken from the shoulder and knee joints of male rabbits (New Zealand White Rabbit) (body weight of 1 to 1.5 kg) under the sterile condition. The cartilages were thoroughly washed with PBS(−) (Ca$^{2+}$, Mg$^{2+}$ free), Hanks' solution and finally 0.1% EDTA-PBS(−), and then, cut into small segments (1 mm×1 mm×1 mm). After PBS(−) containing 0.1% EDTA was added, the segments were incubated at 37° C. for 30 minutes. Then, the segments were treated with trypsin solution (0.25%) at 37° C. for one hour to remove the connective tissues attached to the cartilages. After the supernatant had been removed, the cartilages were treated in a Ham F-12 medium containing 10% fetal bovine serum (FBS) and 0.2% collagenase for approximately 2 to 2.5 hours. Thereafter, the collagenase solution was removed by centrifugation (1500 r.p.m.), the residue was washed twice with Ham medium containing 10% FBS (chondrocyte culture medium). The resulting cell dispersion was adjusted so that the chondrocytes were suspended in the concentration of 3×10$^5$ cells/ml in the chondrocyte culture medium. The chondrocytes were seeded in an amount of 1 ml/well on 24-well plates. The chondrocytes became confluent after 4 days. The experiments were performed within 2 weeks after reaching this stage.

(b) Addition of compounds to be tested and proteoglycan depleting agents

The chondrocyte culture medium which had been used for cultivating the chondrocytes was removed from each well, and 800 μl of fresh serum-free S-Clone (Sanko Junyaku, Tokyo, Japan) medium containing 0.1% human serum albumin was added. Further, 100 μl of S-Clone medium containing the compounds to be tested in various concentrations (containing the compound in the concentration of 10 folds the final concentration; DMSO=2.5%) was added. The chondrocytes were cultured in the presence of 5% carbon dioxide and 95% air for 2 hours. Then, the proteoglycan depleting agent, PMA (phorbol myristate acetate) (final concentration=0.1 μg/ml) or interleukin-1α (IL-1α) (final concentration=20 u/ml) was added into the culture medium of the chondrocytes.

The compounds to be tested were as follows:

Compound of the present invention: esculetin (Tokyo Kasei), 4-methylesculetin (Sigma Chemical Company), 4-methylesculetin 6,7-bis(acetate), 4-methylesculetin 6,7-bis(stearate), 4-methylesculetin 6,7-bis(linoleate), 4-methylesculetin 6,7-bis(docosahexaenoate), esculetin 6,7-bis(benzoate), 4-methylesculetin 6,7-bis(benzoate), esculetin 6,7-bis(acetate), esculetin 6,7-bis(pivalate), and esculetin 6-monopivalate. All of the above compounds were prepared in Example 1 except esculetin and 4-methylesculetin.

Comparative substance: Indomethacin (Sigma Chemical Company)

(c) Determination of proteoglycan

Proteoglycan depletion was determined by the measurement of the glycosaminoglycan (major constituent of proteoglycan, hereinafter referred to as GAG) content following digestion of the chondrocyte matrix with papain.

After 2 days, the supernatant of the chondrocyte culture was removed. Then, 1 ml of 0.03% papain solution was added to the remaining chondrocyte matrix layer and a reaction was performed at 65° C. for 1 hour to liberate the GAG from the matrix layer. The content of the GAG in the treated papain solution was determined by the 1,9-dimethylmethylene blue method (refer to R. W. Farndale, Blochim. Biophys. Acta., Vol. 883, pp. 173 to 177, 1986).

The GAG content in the chondrocyte matrix of the control test wherein the proteoglycan depleting agent was not added was shown as "100", and the relative amount of the GAG of each experiment except the control test was calculated by the following formula:

*GAG relative amount (%)=(B/A)×100* wherein A represents the GAG content of the control tests wherein the proteoglycan depleting agent was not added, and B represents the GAG content wherein the proteoglycan depleting agents were added alone or the GAG content wherein the proteoglycan depleting agents and the compounds to be tested were added.

The GAG contents of the control tests varied in a range of 10.9 to 99.9 μg/ml, depending on the period from the time when the chondrocytes became confluent until the time when the chondrocytes were used in the above experiment.

The results are shown in Table 1. The content of the GAG in the table is the value of the mean value ± standard error (n=3). For each of the compounds to be tested, the control test and the proteoglycan depleting test wherein the proteoglycan depleting agent was added were carried out and the results thereof are also shown. The significance was determined by Student's t-test with respect to the proteoglycan depleting test wherein the proteoglycan depleting agent was added. The results of the determination are shown as follows:

*: P<0.05;
**: P<0.01;
***: P<0.001.

In comparison with the GAG content in the control tests wherein the proteoglycan depleting agent was not added, the addition of the proteoglycan depleting agents, PMA or IL-1α, induced a loss of GAG content. Under these conditions, the present compound inhibited or reduced the loss of GAG content, and showed a function to inhibit or suppress the proteoglycan depletion. To the contrary, indomethacin, a conventional analgesic and anti-inflammatory agent, did not show the function to inhibit or suppress the proteoglycan depletion, but showed a function to exacerbate the cartilage destruction.

TABLE 1

| Samples | GAG content (μg/ml) | (Relative amount of GAG) (%) |
|---|---|---|
| Control | 72.1 ± 3.20*** | (100) |
| IL-1α | 37.8 ± 2.21 | (52.4) |
| +esculetin 100 μM | 63.9 ± 3.80** | (88.6) |
| Control | 58.8 ± 2.60*** | (100) |
| PMA | 37.9 ± 1.37 | (64.5) |
| +esculetin 100 μM | 78.0 ± 2.32*** | (133) |
| Control | 99.9 ± 1.10*** | (100) |
| PMA | 59.1 ± 0.80 | (59.2) |
| +4-methylesculetin 100 μM | 72.1 ± 0.70*** | (72.2) |
| Control | 20.3 ± 2.33*** | (100) |
| IL-1α | 14.3 ± 2.57 | (70.4) |
| +4-methylesculetin 6,7-bis(acetate) 100 μM | 27.3 ± 3.66* | (134) |
| Control | 39.7 ± 0.55** | (100) |
| IL-1α | 33.0 ± 0.55 | (83.1) |
| +4-methylesculetin 6,7-bis(linoleate) 100 μM | 37.3 ± 0.73** | (94.0) |
| +4-methylesculetin 6,7-bis(stearate) 100 μM | 43.7 ± 0.37*** | (110) |
| +4-methylesculetin 6,7-bis(docosahexaenoate) 100 μM | 43.0 ± 0.12*** | (108) |
| +4-methylesculetin 6,7-bis(benzoate) 100 μM | 44.7 ± 0.93*** | (113) |
| Control | 10.9 ± 0.23** | (100) |
| IL-1α | 8.71 ± 0.23 | (79.9) |
| +esculetin 6,7-bis(benzoate) 100 μM | 9.54 ± 0.15* | (87.5) |
| Control | 24.3 ± 3.33*** | (100) |
| PMA | 11.3 ± 1.76 | (46.5) |
| +4-methylesculetin 6,7-bis(acetate) 100 μM | 25.4 ± 3.84** | (105) |
| Control | 44.3 ± 0.61*** | (100) |
| PMA | 37.9 ± 1.67 | (85.6) |
| +4-methylesculetin 6,7-bis(linoleate) 100 μM | 42.3 ± 0.82* | (95.5) |
| +4-methylesculetin 6,7-bis(stearate) 100 μM | 47.0 ± 1.10** | (106) |
| +4-methylesculetin 6,7-bis(docosahexaenoate) 100 μM | 47.6 ± 0.49** | (108) |
| +4-methylesculetin 6,7-bis(benzoate) 100 μM | 48.1 ± 1.56* | (109) |
| Control | 24.0 ± 0.44*** | (100) |
| 1L-1α | 16.0 ± 0.68 | (66.7) |
| +esculetin | 20.9 ± 1.86 | (87.1) |

TABLE 1-continued

| Samples | GAG content (μg/ml) | (Relative amount of GAG) (%) |
|---|---|---|
| 6,7-bis(acetate) 100 μM | | |
| +esculetin 6,7-bis(pivalate) 10 μM | 19.2 ± 1.58 | (80.0) |
| +esculetin 6-monopivalate 100 μM | 21.8 ± 2.19* | (90.8) |
| Control | 28.0 ± 0.7*** | (100) |
| PMA | 15.4 ± 0.5 | (55.0) |
| +indomethacin 10 | 13.2 ± 0.6* | (47.1) |
| 33 μM | 11.7 ± 0.8** | (41.8) |

Example 4: Formulation of Granule

The following ingredients were mixed homogeneously:

| Esculetin | 20 parts by weight |
|---|---|
| Lactose | 68 parts by weight |
| Low-substituted | |
| Hydroxypropylcellulose | 10 parts by weight |
| Hydroxypropylcellulose | 2 parts by weight |

The mixture was kneaded using 32 parts by weight of a wetting agent, ethanol. Then, the kneaded mixture was granulated by wet granulation and dried to obtain the granule.

As explained above, the present compound (I) strongly inhibits proteoglycan depletion from the chondrocyte matrix and exhibits a function to protect cartilage. Further, the present compound (I) has low toxicity. Accordingly, the present compound (I) is extremely effective for the treatment of arthropathy, such as rheumatoid arthritis, osteoarthritis, periarthritis humeroscapularis, shoulder-arm-neck syndrome, lumbago, and so on.

Although the present invention has been described with reference to specific embodiments, various changes and modifications obvious to those skilled in the art are deemed to be within the spirit, scope, and concept of the invention.

I claim:

1. A pharmaceutical composition, comprising a compound of the formula (I):

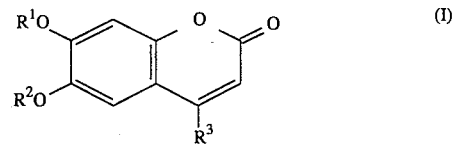

wherein $R^1$ and $R^2$ are, independently, a hydrogen atom, a saturated or unsaturated aliphatic acyl having 2 to 25 carbon atoms or a benzoyl group, and $R^3$ is a hydrogen atom or an alkyl group, and a pharmaceutically acceptable carrier, with the proviso that when $R^3$ is a hydrogen atom, $R^1$ and $R^2$ are not hydrogen atoms or acetyl groups at the same time, or when $R^3$ is a methyl group, $R^1$ and $R^2$ are not hydrogen atoms, acetyl groups, palmitoyl groups, capryloyl groups or lauroyl groups at the same time.

2. A pharmaceutical composition according to claim 1, wherein $R^1$ and $R^2$ are, independently, a hydrogen atom, an acetyl group, a pivaloyl group, a capryloyl group, a lauroyl group, a palmitoyl group, a stearoyl group, a linoleoyl group, a docosahexaenoyl group, or a benzoyl group, and $R^3$ is a hydrogen atom or a lower alkyl group having 1 to 4 carbon atoms.

3. A pharmaceutical composition according to claim 2, wherein $R^1$ and $R^2$ are, independently, a hydrogen atom, a pivaloyl group, a capryloyl group, a lauroyl group, a palmitoyl group, a stearoyl group, a linoleoyl group, a docosahexaenoyl group, or a benzoyl group, and $R^3$ is a hydrogen atom or a methyl group.

4. A pharmaceutical composition according to claim 3, wherein $R^1$ and $R^2$ are, independently, a hydrogen atom, a pivaloyl group, a stearoyl group, or a benzoyl group.

5. A method for treating arthropathy, comprising administering to a mammal in need thereof an arthropathy treating effective amount of a compound of the formula (I):

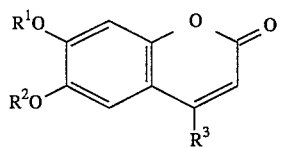
(I)

wherein $R^1$ and $R^2$ are, independently, a hydrogen atom, a saturated or unsaturated aliphatic acyl having 2 to 25 carbon atoms or a benzoyl group, and $R^3$ is a hydrogen atom or an alkyl group.

6. A method for treating arthropathy according to claim 5, wherein $R^1$ and $R^2$ are independently, a hydrogen atom, an acetyl group, a pivaloyl group, a capryloyl group, a lauroyl group, a palmitoyl group, a stearoyl group, a linoleoyl group, a docosahexaenoyl group, or a benzoyl group, and $R^3$ is a hydrogen atom or a lower alkyl group having 1 to 4 carbon atoms.

7. A method for treating arthropathy according to claim 6, wherein $R^1$ and $R^2$ are, independently, a hydrogen atom, a pivaloyl group, a capryloyl group, a lauroyl group, a palmitolyl group, a stearoyl group, a linoleoyl group, a docasahexaenoyl group, or a benzoyl group, and $R^3$ is a hydrogen atom or a methyl group.

8. A method for treating arthropathy according to claim 7, wherein $R^1$ and $R^2$ are, independently, a hydrogen atom, a pivaloyl group, a stearoyl group or a benzoyl group.

9. A method for treating arthropathy according to claim 5, wherein the compound is selected from the group consisting of esculetin, 4-methylesculetin, esculetin 6,7-bis(acetate), 4-methylesculetin 6,7-bis(acetate), esculetin 6,7-bis(pivalate), 4-methylesculetin 6,7-bis(pivalate), esculetin 6-monopivalate, 4-methylesculetin 6-monopivalate, esculetin 7-monopivalate, 4-methylesculetin 7-monopivalate, esculetin 6,7-bis(caprylate), 4-methylesculetin 6,7-bis(caprylate), esculetin 6,7-bis(laurate), 4-methylesculetin 6,7-bis(laurate), esculetin 6,7-bis(palmitate), 4-methylesculetin 6,7-bis(palmirate), esculetin 6,7-bis(stearate), 4-methylesculetin 6,7-bis(stearate), esculetin 6,7-bis(linoleate), 4-methylesculetin 6,7-bis(linoleate), esculetin 6,7-bis(docosahexaenoate), 4-methylesculetin 6,7-bis(docosahexaenoate), and esculetin 6,7-bis(benzoate), 4-methylesculetin 6,7-bis(benzoate).

10. A method for treating arthropathy according to claim 9, wherein the compound is selected from the group consisting of esculetin 6-monopivalate, esculetin 6,7-bis(pivalate), esculetin 6,7-bis(stearate), 4-methylesculetin 6,7-bis(stearate), 4-methylesculetin 6,7-bis(linoleate), 4-methylesculetin 6,7-bis(docosahexaenoate) and 4-methylesculetin 6,7-bis(benzoate).

11. A method for protecting cartilage, comprising administering to a mammal in need thereof a cartilage protecting amount of a compound of formula (I):

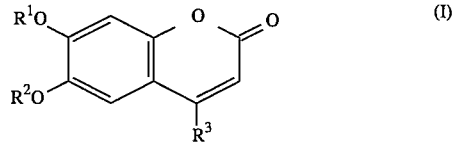
(I)

wherein $R^1$ and $R^2$ are, independently, a hydrogen atom, a saturated or unsaturated aliphatic acyl having 2 to 25 carbon atoms or a benzoyl group, and $R^3$ is a hydrogen atom or an alkyl group.

12. A method for protecting cartilage according to claim 11, wherein $R^1$ and $R^2$ are independently, a hydrogen atom, an acetyl group, a pivaloyl group, a capryloyl group, a lauroyl group, a palmitoyl group, a stearoyl group, a linoleoyl group, a docosahexaenoyl group, or a benzoyl group, and $R^3$ is a hydrogen atom or a lower alkyl group having 1 to 4 carbon atoms.

13. A method for protecting cartilage according to claim 12, wherein $R^1$ and $R^2$ are, independently, a hydrogen atom, a pivaloyl group, a capryloyl group, a lauroyl group, a palmitolyl group, a stearoyl group, a linoleoyl group, a docasahexaenoyl group, or a benzoyl group, and $R^3$ is a hydrogen atom or a methyl group.

14. A method for protecting cartilage according to claim 13, wherein $R^1$ and $R^2$ are, independently, a hydrogen atom, a pivaloyl group, a stearoyl group or a benzoyl group.

15. A method for protecting cartilage according to claim 11, wherein the compound is selected from the group consisting of esculetin, 4-methylesculetin, esculetin 6,7-bis(acetate), 4-methylesculetin 6,7-bis(acetate), esculetin 6,7-bis(pivalate), 4-methylesculetin 6,7-bis(pivalate), esculetin 6-monopivalate, 4-methylesculetin 6-monopivalate, esculetin 7-monopivalate, 4-methylesculetin 7-monopivalate, esculetin 6,7-bis(caprylate), 4-methylesculetin 6,7-bis(caprylate), esculetin 6,7-bis(laurate), 4-methylesculetin 6,7-bis(laurate), esculetin 6,7-bis(palmitate), 4-methylesculetin 6,7-bis(palmirate), esculetin 6,7-bis(stearate), 4-methylesculetin 6,7-bis(stearate), esculetin 6,7-bis(linoleate), 4-methylesculetin 6,7-bis(linoleate), esculetin 6,7-bis(docosahexaenoate), 4-methylesculetin 6,7-bis(docosahexaenoate), and esculetin 6,7-bis(benzoate), 4-methylesculetin 6,7-bis(benzoate).

16. A method for protecting cartilage according to claim 15, wherein the compound is selected from the group consisting of esculetin 6-monopivalate, esculetin 6,7-bis(pivalate), esculetin 6,7-bis(stearate), 4-methylesculetin 6,7-bis(stearate), 4-methylesculetin 6,7-bis(linoleate), 4-methylesculet in 6,7-bis(docosahexaenoate) and 4-methylesculetin 6,7-bis(benzoate).

* * * * *

UNITED STATES PATENT AND TRADEMARK OFFICE
CERTIFICATE OF CORRECTION

PATENT NO. : 5,455,268
DATED : October 3, 1995
INVENTOR(S) : Koju Watanabe, et al.

It is certified that error appears in the above-indentified patent and that said Letters Patent is hereby corrected as shown below:

On the title page, item [54] and column 1, line 1:

In the title, before "ESCULETIN" insert --NOVEL--.

Column 2, at both occurrences, change:

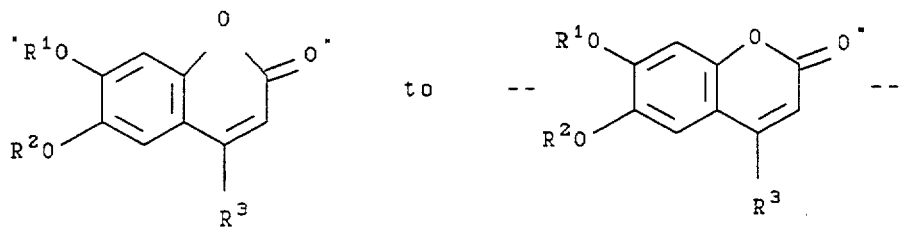

Column 3, line 23, change "and-methylesculetin" to --and 4-methylesculetin--, and line 33, change "and" to --with--.

UNITED STATES PATENT AND TRADEMARK OFFICE
CERTIFICATE OF CORRECTION

PATENT NO. : 5,455,268
DATED : October 3, 1995
INVENTOR(S) : Koju Watanabe, et al.

It is certified that error appears in the above-indentified patent and that said Letters Patent is hereby corrected as shown below:

Column 5, line 25, change "6,7-bis(acetate)" to --6,7-bis(stearate)--;

line 45, change "85°- 860°C" to --85° - 86°C--; and line 54, change "121° - 1220°C" to --121° - 122°C--.

Column 6, line 62, change "rag" to --mg--.

Column 9, line 10, change "To" to --On--.

Column 10, delete the table of lines 20-27 and insert:

| | |
|---|---|
| Esculetin | 20 parts by weight |
| Lactose | 68 parts by weight |
| Low-substituted Hydroxypropylcellulose | 10 parts by weight |
| Hydroxypropylcellulose | 2 parts by weight |

UNITED STATES PATENT AND TRADEMARK OFFICE
CERTIFICATE OF CORRECTION

PATENT NO. : 5,455,268
DATED : OCTOBER 3, 1995
INVENTOR(S) : Koju WATANABE et al.

It is certified that error appears in the above-indentified patent and that said Letters Patent is hereby corrected as shown below:

Columns 10, and 11:

Claims 1, 5 and 11, change:

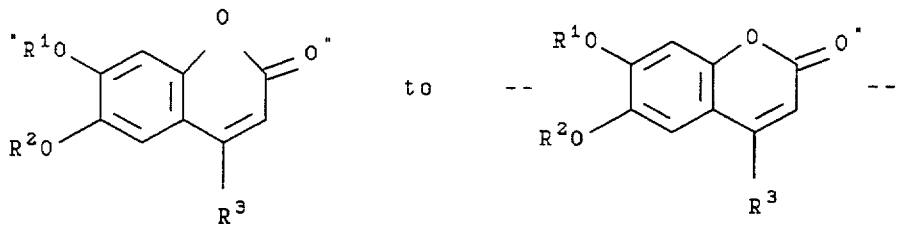

Column 11:
  Claim 9, line 11, change "6,7-bis(palmirate)" to --6,7-bis(palmitate)--.
Column 12:
  Claim 15, line 11, change "6,7-bis(palmirate)" to --6,7-bis(palmitate)--.

Claim 16, lines 5 and 6, change "4-methylesculet in" to --4-methylesculetin--.

UNITED STATES PATENT AND TRADEMARK OFFICE
CERTIFICATE OF CORRECTION

PATENT NO. : 5,455,268
DATED : October 3, 1995
INVENTOR(S) : Koju Watanabe, et al.

It is certified that error appears in the above-indentified patent and that said Letters Patent is hereby corrected as shown below:

Column 12, claim 16, lines 5 and 6, change "4-methylesculet in" to --4-methylesculetin--.

Signed and Sealed this

Eighth Day of October, 1996

*Attest:*

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO. : 5,455,268
DATED : OCTOBER 3, 1995
INVENTOR(S) : Koju WATANABE et al.

It is certified that error appears in the above-indentified patent and that said Letters Patent is hereby corrected as shown below:

In the Abstract of the Disclosures, change:

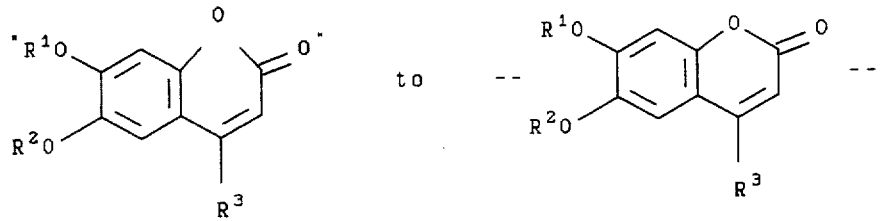

Signed and Sealed this

Twelfth Day of November, 1996

Attest:

BRUCE LEHMAN

*Attesting Officer*  *Commissioner of Patents and Trademarks*